(12) United States Patent
Xu et al.

(10) Patent No.: US 12,702,355 B2
(45) Date of Patent: Aug. 11, 2026

(54) WEARABLE DEVICE FOR MONITORING FLUID OVERLOAD WITH BUILT-IN SENSORS

(71) Applicant: Bard Peripheral Vascular, Inc., Franklin Lakes, NJ (US)

(72) Inventors: Qihua Xu, Cary, NC (US); Andrzej J. Chanduszko, Chandler, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 219 days.

(21) Appl. No.: 18/284,050

(22) PCT Filed: Apr. 1, 2022

(86) PCT No.: PCT/US2022/023154
§ 371 (c)(1),
(2) Date: Sep. 25, 2023

(87) PCT Pub. No.: WO2022/225679
PCT Pub. Date: Oct. 27, 2022

(65) Prior Publication Data

US 2024/0172995 A1 May 30, 2024

Related U.S. Application Data

(60) Provisional application No. 63/178,426, filed on Apr. 22, 2021.

(51) Int. Cl.
*A61B 5/00* (2006.01)
*G16H 10/60* (2018.01)

(52) U.S. Cl.
CPC .......... *A61B 5/4878* (2013.01); *A61B 5/6824* (2013.01); *A61B 5/6829* (2013.01);
(Continued)

(58) Field of Classification Search
CPC ... A61B 5/4878; A61B 5/6824; A61B 5/6829; A61B 5/6831; A61B 5/6832;
(Continued)

(56) References Cited

U.S. PATENT DOCUMENTS

2014/0378785 A1* 12/2014 Wekell .................. A61B 5/1118 600/595
2015/0182163 A1* 7/2015 Utter ........................ A61B 5/08 600/595

(Continued)

FOREIGN PATENT DOCUMENTS

WO 2022225679 A1 10/2022

OTHER PUBLICATIONS

PCT/US2022/023154 filed Apr. 1, 2022 International Search Report and Written Opinion dated Sep. 9, 2022.

*Primary Examiner* — Carl H Layno
*Assistant Examiner* — Aya Ziad Bakkar
(74) *Attorney, Agent, or Firm* — Rutan & Tucker LLP

(57) ABSTRACT

A wearable device for monitoring a tissue swelling condition of a user is disclosed that includes a device attachment mechanism for securing the device to the user, and a sensing mechanism coupled to the attachment mechanism. The sensing mechanism can be configured to provide an electrical signal in accordance with the tissue swelling condition of the user to a console, where the console can be configured to: (i) receive the electrical signal from the sensing mechanism, and (ii) provide swelling information to the user in accordance with the electrical signal. Various tissue swelling sensing mechanisms are disclosed, as well as a system including the wearable device and storage, where the storage includes executable instructions that when executed by one or more processors causes the one or more processors to perform operations, including receiving tissue swelling data
(Continued)

from the wearable device, and rendering tissue swelling information on a display.

18 Claims, 8 Drawing Sheets

(52) U.S. Cl.
CPC .......... *A61B 5/6831* (2013.01); *A61B 5/6832* (2013.01); *A61B 5/6843* (2013.01); *A61B 5/743* (2013.01); *A61B 5/746* (2013.01); *G16H 10/60* (2018.01)

(58) Field of Classification Search
CPC ....... A61B 5/6843; A61B 5/743; A61B 5/746; A61B 5/4881; G16H 10/60
See application file for complete search history.

(56) References Cited

U.S. PATENT DOCUMENTS

| | | | | |
|---|---|---|---|---|
| 2015/0313533 | A1* | 11/2015 | Rapp | A61B 5/0082<br>600/476 |
| 2016/0073949 | A1* | 3/2016 | Grant | A61B 5/742<br>600/407 |
| 2018/0064392 | A1 | 3/2018 | Ur et al. | |
| 2018/0220961 | A1 | 8/2018 | Burns et al. | |
| 2019/0117156 | A1 | 4/2019 | Howard et al. | |
| 2020/0054279 | A1 | 2/2020 | Krupnick et al. | |

* cited by examiner

FIG. 3B 360
330
Health Care Provider
320
100,362
301
100,362

700
720
731
715
723
714A
715A
722
61
714
725
721
723A
60

800
820
832
821
833
825
831
814
814A
830
60

WEARABLE DEVICE FOR MONITORING FLUID OVERLOAD WITH BUILT-IN SENSORS

PRIORITY

This application is a U.S. national stage application of International Application No. PCT/US2022/023154, filed Apr. 1, 2022, which claims the benefit of priority to U.S. Provisional Application No. 63/178,426, filed Apr. 22, 2021, each of which is incorporated by reference in its entirety into this application.

BACKGROUND

Edema (or swelling) can occur due to a variety of medical reasons. Edema is swelling caused by excess fluid trapped in the body's tissues and is most common in the feet, legs, hands, and face. Edema typically occurs in response to injury or inflammation, but edema can also occur as a result of a number of medical conditions, including heart disease (congestive heart failure), preeclampsia, liver disease, kidney disease, lymphedema, critical illnesses, and in response to medications. Swelling can also occur in heart failure (HF) patients preceding an acute decompensated heart failure (ADHF) event: a gradual increase in total body water, lower extremity edema, weight changes, reduced activity levels, and alterations in autonomic function (e.g., heart rate variability). Typically, there are three major methods for prediction of ADHF event. Assessment of weight can be used as a surrogate of fluid retention, but this method lacks sensitivity and specificity. Adhesive skin devices attached to the upper thorax can be used for monitoring but are found uncomfortable to use among HF patients. Implantable cardiac devices can provide certain measurements, but such devices are too expensive and invasive to be accessible to most of the HF population. Wearable devices such as those included herein may be relatively inexpensive and non-invasive solutions that can provide continuous home monitoring of swelling and predict impending decompensation in HF patients.

SUMMARY

Briefly summarized, disclosed herein is a wearable device for monitoring a tissue swelling condition of a user or "wearer." The wearable device includes a device attachment mechanism for securing the device to the body of the user, a sensing mechanism coupled to the attachment mechanism, where the sensing mechanism is configured to provide an electrical signal in accordance with the tissue swelling condition of the user, and logic, that, upon execution by one or more processors, causes performance of operations that include receiving the electrical signal from the sensing mechanism, and providing swelling information to the user in accordance with the electrical signal. In some embodiments, the attachment mechanism includes a band configured to extend around an extremity of the user, where the extremity may be an ankle or a wrist of the user. In some embodiments, attachment mechanism is configured to secure the device to the body of the user via one or more adhesive portions.

In some embodiments, the sensing mechanism may provide the electrical signal in accordance with a physical dimension of the attachment mechanism. The attachment mechanism may include a stretchable portion, and the physical dimension may be a length of the stretchable portion. The sensing mechanism may include a sensor coupled to the stretchable portion, and the sensor may be configured to provide the electrical signal in accordance a length of the stretchable portion.

In some embodiments, the attachment mechanism includes a light sensor operatively coupled with a light source and a variable aperture disposed between the light source and the light sensor. The aperture may vary in accordance a length of a stretchable portion of the attachment mechanism, and the light sensor may provide the electrical signal in accordance with an amount of light from the light source passing through the variable aperture to the light sensor. The variable aperture may include a first opening extending through a first portion of the attachment mechanism and a second opening extending through a second portion of the attachment mechanism, where the first portion overlaps the second portion. In such embodiments, the first portion and the second portion may be coupled to opposite ends of the stretchable portion of the attachment mechanism, so that the second portion is displaced relative to the first portion in accordance with a change in the length of the stretchable portion, and the first and second openings are positioned to variably overlap in accordance with the relative displacement between the second portion and the first portion to define the variable aperture.

In some embodiments, the sensing mechanism provides the electrical signal in accordance with a space between the user's skin and the attachment mechanism. In some embodiments, the sensing mechanism includes a fluid containing bladder disposed within the space between the user's skin and the attachment mechanism such that tissue swelling causes the bladder to collapse. The fluid channel is in fluid communication with the bladder, such that collapsing the bladder displaces fluid along the channel, and a sensor may be operatively coupled to the channel, so that the sensor is configured to provide the electrical signal in accordance with a volume of fluid disposed within the channel.

In some embodiments, the sensing mechanism includes a pressure sensor disposed between the user's skin and the attachment mechanism, where the pressure sensor is configured to provide the electrical signal in accordance with a pressure exerted on the sensor by the skin.

In some embodiments, the sensing mechanism includes a device for creating a tissue depression on the user and a sensor configured to measure a depression depth as the tissue recovers toward a non-depressed state. The sensor is configured to provide the electrical signal in accordance with a recovery rate of the depression. The device for creating the tissue depression may include an inflatable bladder disposed between the user's skin and the attachment mechanism, where the bladder is configured for selective inflation and deflation between a protruding state and a collapsed state, such that upon inflation, the bladder protrudes inward away from the attachment mechanism to create the tissue depression, and upon deflation, the depression is allowed to recover toward the non-depressed state. The sensor may be a proximity sensor coupled with the attachment mechanism so as to define a proximity sensing region extending to a depth of the depression, and the proximity sensor may be configured to provide the electrical signal in accordance with the depth of the depression.

The logic may include a swelling logic module stored in memory and the swelling logic module is configured to: (i) compare swelling data with a swelling limit stored in memory, and (ii) as a result of the comparison, provide an alert to the user.

The logic may further include a correlation module stored in memory. The correlation module may be configured to receive independent tissue swelling assessments as input by the user, correlate the swelling data with the independent assessments, and display swelling information in accordance with the correlation.

In some embodiments, the wearable device includes the one or more processors, and in other embodiments, the one or more processors are included within cloud computing resources.

Further disclosed herein is a system for monitoring tissue swelling of a user. The system includes the wearable device as summarized above and a non-transitory computer-readable storage medium (CRM) including executable instructions that when executed by one or more processors causes the one or more processors to perform operations. The operations include receiving tissue swelling data from the wearable device, and rendering tissue swelling information on a display. The CRM may be stored on a cellular phone.

The operations may further include comparing the swelling data with a swelling limit stored in the CRM. As a result of the comparison, the operations may generate a user alert.

The operations may further include maintaining a historical record of the swelling data and the operations may include rendering a chart on the display, where the chart illustrates at least a portion of the historical swelling data record.

The operations may further include receiving independent tissue swelling assessments as input by the user, correlating the swelling data to the independent assessments, and displaying swelling information in accordance with the correlation.

The operations may further include receiving user event information as input by the user, where the information includes one or more user events. The operations may further include correlating the swelling data to the user events, and displaying historical swelling information in combination with the user event information.

In some embodiments, the operations further include transmitting the user information across a network to an external entity, and the external entity may be a healthcare provider for the user.

These and other features of the concepts provided herein will become more apparent to those of skill in the art in view of the accompanying drawings and the following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 3B illustrates a flow chart of a computerized process of the system of FIG. 3A, in accordance with some embodiments disclosed herein;

DESCRIPTION

Figure 1:
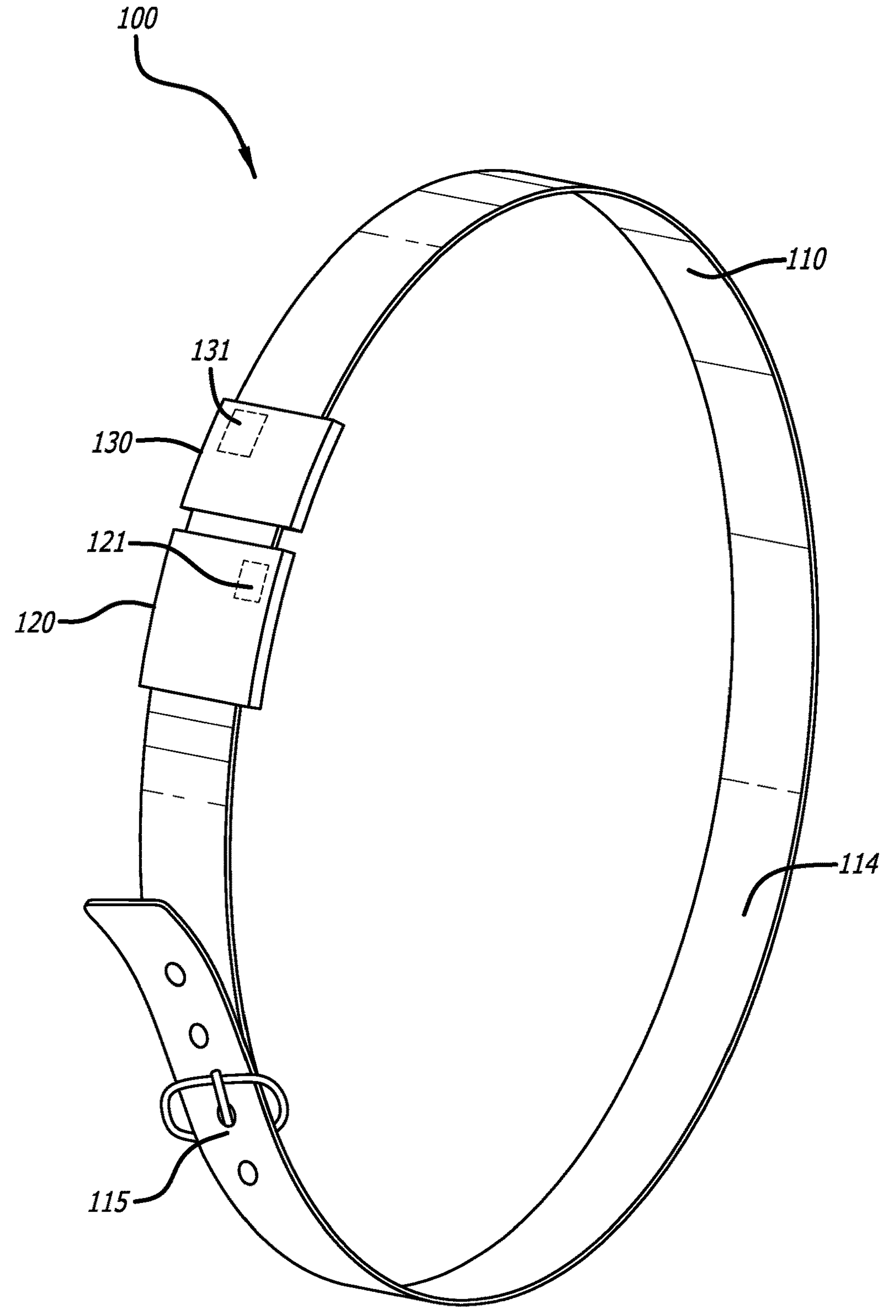
FIG. 1 illustrates a wearable device for monitoring tissue swelling, in accordance with some embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The phrases "connected to" and "coupled with" refer to any form of interaction between two or more entities, including mechanical, electrical, magnetic, electromagnetic, fluid, and thermal interaction. Two components may be connected or coupled with each other even though they are not in direct contact with each other. For example, two components may be coupled with each other through an intermediate component.

The directional terms "proximal" and "distal" are used herein to refer to opposite locations on a medical device. The proximal end of the device is defined as the end of the device closest to the end-user when the device is in use by the end-user. The distal end is the end opposite the proximal end, along the longitudinal direction of the device, or the end furthest from the end-user. The term "fluid" is used herein to refer to either a gas or a liquid.

In certain situations, the term "logic" is representative of hardware, firmware, and/or software that is configured to perform one or more functions. As hardware, the logic may include circuitry having data processing or storage functionality. Examples of such circuitry may include, but are not limited or restricted to a microprocessor, one or more processor cores, a programmable gate array, a microcontroller, an application specific integrated circuit, wireless receiver, transmitter and/or transceiver circuitry, semiconductor memory, or combinatorial logic.

Alternatively, or in combination with the hardware circuitry described above, the logic may be software in the form of one or more software modules. The software module(s) may include an executable application, an application programming interface (API), a subroutine, a function, a procedure, an applet, a servlet, a routine, source code, a shared library/dynamic load library, or one or more instructions. The software module(s) may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; a semiconductor memory; non-persistent storage such as volatile memory (e.g., any type of random access memory "RAM"); persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the executable code may be stored in persistent storage. Further, the term "computerized" generally represents that any corresponding operations are conducted by hardware in combination with software and/or firmware.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

FIG. 1 illustrates an exemplary wearable device 100 to monitor tissue swelling of a user. The device 100 includes a user attachment mechanism 110, a sensing mechanism 120, and a console 130. In the illustrated embodiment, the attachment mechanism 110 includes a band 114 and a band securement device 115. The band 114 may be sized to extend around an extremity of a user such as an arm or a leg and the securement device 115 may be configured to selectively attach one portion of the band 114 to another portion of the band 114. The sensing mechanism 120 may be attached to the band 114 or the sensing mechanism 120 may define a portion of the band 114. The console 130 is attached to the band 114 and may include various electrical components including swelling logic 131 as further described below.

The band 114 may be configured to accommodate a range of extremity sizes. For example, the band 114 may define a length so as to extend along a range of extremity circumferences. In some embodiments, the securement device 115 may define a range of discreet circumferential lengths of the band 114, so that in use, the attachment mechanism 110 may operatively couple with extremities having a range of circumferences. The securement device may include a buckle, a cinching ring, a hook and loop fastener, or any other suitable mechanism for securing (i.e., fixing or attaching) one portion of the band 114 to other portion of the band.

In some embodiments, the attachment mechanism 110 may be non-stretchable during use. In other words, the attachment mechanism 110 may be configured to maintain one or more fixed lengths when the attachment mechanism 110 is placed under tension. For example, the band 114 in combination with the securement device 115 may define a fixed (non-stretchable) circumferential length so as to withstand any applied hoop stress during use without increasing in length. In such embodiments, a tensile stress in the attachment mechanism 110 may correlate with a pressure applied to the attachment mechanism 110. For example, a hoop stress of the band 114 may substantially correlate with a swelling condition of the extremity.

In other embodiments, the attachment mechanism 110 may be substantially stretchable so that a dimensional change of the extremity may correlate to a dimensional change of the attachment mechanism 110. For example, an increase in a circumference of the extremity may substantially correlate with an increase in a circumferential length of the band 114.

In some embodiments, the stretchable nature of the attachment mechanism 110 may facilitate operative coupling to the extremity. In some embodiments, the attachment mechanism 110 may include band 114 forming a closed loop, i.e., the securement device 115 may be omitted. In such an embodiment, the loop may sufficiently stretch over a portion of the extremity. By way of example, the loop may sufficiently stretch to allow passage of a hand through the loop and then revert back to a reduced stretched state for operative coupling to a wrist.

In some embodiments, the attachment member 110 may be formed of a sock, ring, glove, etc. In some embodiments, the attachment member 110 may be patch (e.g., a two-dimensional patch) adhesively applied to the skin of the user.

The attachment mechanism 110 is configured to operatively couple the sensing mechanism 120 to the user. In other words, the attachment mechanism 110 facilitates assessment of a tissue-swelling condition of the user by the sensing mechanism 120. The sensing mechanism 120 includes at least one swelling sensor 121.

Figure 2:
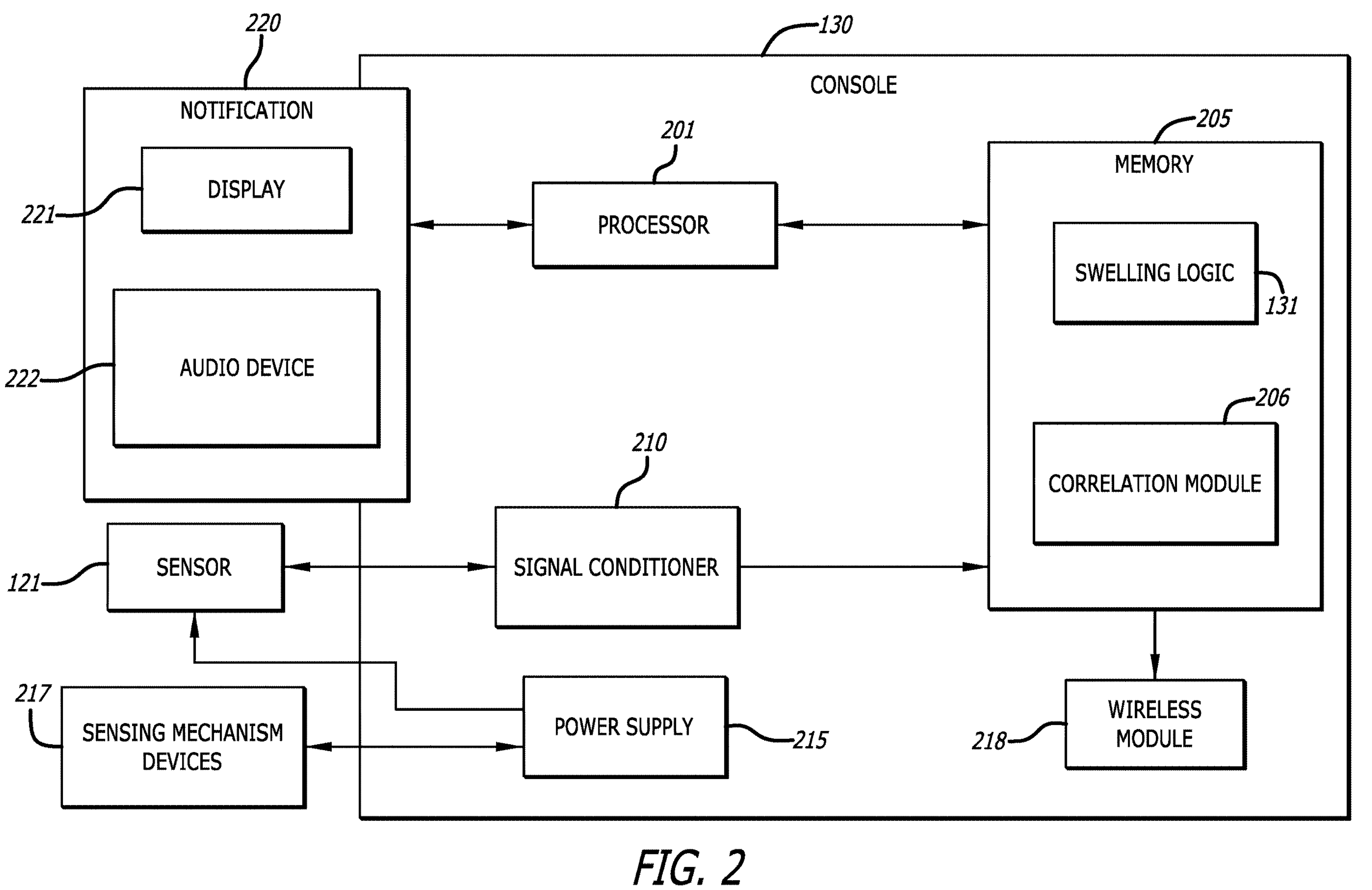
FIG. 2 is a block diagram of a console of the wearable device of FIG. 1, in accordance with some embodiments disclosed herein.

FIG. 2 is a block diagram of various components of the console 130 as shown in FIG. 1. The console 130 is configured to convert raw electrical signals provided by the sensor 121 into useable swelling information for the user. The console 130 includes a power supply 215 to provide electrical power to the other modules, the sensor 121 and any other sensing mechanism devices 217. The raw electrical signals passed from the sensor 121 through the signal conditioner 210 to the swelling logic 131 stored in memory 205 which includes non-transitory computer-readable storage medium. A processor 201 causes operations of the wearable device 100 in accordance with the swelling logic 131 such as notifications to the user via the notification module 220. The notification module 220 may include a display 221 to render visual notifications to the user. In some embodiments, the display 221 may include a graphical user interface (GUI) to receive input information from the user. The notification module 220 may also include an audio device 222 to provide audible notifications to the user. The console 130 may also include a wireless communication module 218 to facilitate communication of the wearable device 100 with external devices as further described below.

As described above the swelling logic 131 may cause operations of the sensing mechanism 120. The swelling logic 131 may process electrical signals obtained from the sensing mechanism 120 into a swelling report for the user. The swelling report may include multiple swelling parameters that may be useful for the user in determining a course of action.

In some embodiments, the report may include a current swelling condition. For example, the report may indicate the current swelling condition on a scale from "low" to "high." The report may also indicate the current direction of the swelling condition, i.e., increasing or decreasing. In some embodiments, the swelling logic 131 may use color to indicate a current swelling condition or trend.

In some embodiments, the report may plot periodic swelling data points over a short period (e.g., over the last few hours or throughout the day) so that the user may interpret a short-term trend. In some embodiments, the report may plot periodic swelling data points over a long period (e.g., over the last few weeks) so that the user may interpret a long-term trend.

In some embodiments, the swelling logic 131 may compare one or more swelling report values with one or more thresholds stored in memory 205. In such an embodiment, the swelling logic 131 may generate an audio and/or a visual alarm to alert the user that a swelling condition exceeds a threshold which may indicate a swelling condition of heightened concern.

In some instances, the sensing mechanism 120 may need to distinguish fluid-overload swelling from another condition such as flexing a muscle, for example. As such, the swelling logic 131 may include data filtering so that conditions associated with flexing a muscle for example, are not interpreted as fluid-overload swelling. Such filtering may include a low-pass filter to eliminate short term (e.g., over a few seconds) conditions from the swelling data.

In some embodiments, the memory 205 may include a correlation module 206. The correlation module 206 may be configured to correlate a swelling condition as measured by the wearable device 100 with an independent swelling assessment. For example, a clinician may perform an edema assessment of the user to determine a level of edema (swelling) and associate the swelling assessment value with a category such as low, medium or high. The user may input the associated category into the wearable device 100. The swelling logic 131 may then correlate the swelling condition as measured by the wearable device 100 with the associated category. In some instances, the user may perform an independent self-assessment of the swelling condition such as with a measuring tape and input an associated category.

Figure 3A:
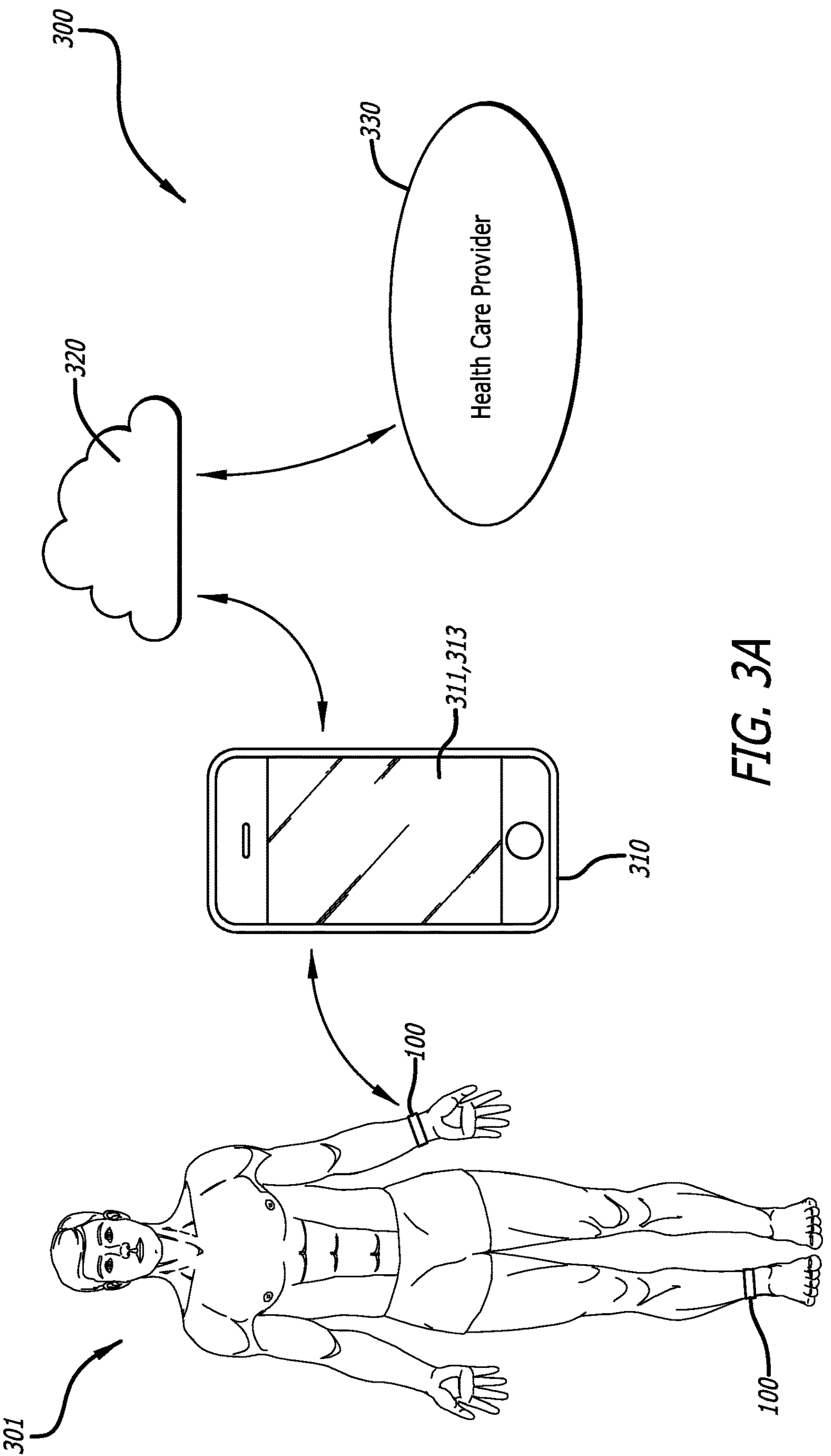
FIG. 3A illustrates a first exemplary embodiment of a system for monitoring tissue swelling incorporating the wearable device of FIG. 1, in accordance with some embodiments disclosed herein.

FIG. 3A illustrates a first exemplary embodiment of a tissue swelling management system including an architecture as illustrated. The architecture of the system 300 may include the wearable device 100, a user device 310 including logic 311 operating thereon, a network 320, and an external entity 330. In some embodiments, the system 300 may include more than one wearable device 100. The network 320 represents the communication pathways between the user device 310 and the external entity 330. In one embodiment, the network 320 is the Internet. The network 320 can also utilize dedicated or private communication links (e.g., WAN, MAN, or LAN) that are not necessarily part of the Internet. The network 320 may use standard communications technologies and/or protocols. In some embodiments, the logic 311 may be in the form of a software application that is loaded on the user device 310 and executable by hardware processing circuitry. In other embodiments, the logic 311 need not be loaded on the user device 310 but may instead execute within a cloud computing environment (which may also be represented by the reference numeral 320) such that data obtained or otherwise detected by sensor(s) of the wearable device 100 are communicated to the logic 311 for processing. Thus, any logic 311 represented as being part of the user device 310 may include an application programming interface (API) that is configured to transmit and receive data communication messages to and from the logic 311 operating in the cloud computing environment.

The user device 310 can be any device that incorporates logic (as well as hardware circuitry and non-transitory, computer-readable memory in instances in which logic refers to software). In some instances, the user device 310 executes an operating system, for example, a MICROSOFT WINDOWS®-compatible operating system (OS), APPLE OS X® or IOS®, a LINUX® distribution, or GOOGLE ANDROID™. In some embodiments, the user device 310 may use a web browser, such as MICROSOFT INTERNET EXPLORER®, MOZILLA FIREFOX, GOOGLE CHROME™, APPLE SAFARI® and/or OPERA®, as an interface to interact with the logic 311.

The user device 310 is communicatively coupled to the wearable device 100 via a wireless protocol, e.g., BLUETOOTH®, radio frequency, infrared, microwave, Zigbee, or any other suitable wireless protocol. In some embodiments, the user device 310 may be coupled to the wearable device 100 via a wired connection. The user device 310 receives tissue swelling information or data from the wearable device 100. The user 301 may provide tissue swelling information to the user device 310 by direct input.

The external entity 330 may be a person, an institution, or a cloud computing environment (e.g., cloud computing resources accessible via a network such as the internet). In some embodiments, the external entity 330 may be family member, a friend or any person for which access to tissue swelling information may be of benefit to the user 301. In some embodiments, the external entity 330 may be a healthcare provider, for which the user 301 may be a patient. As such, it may be advantageous for the healthcare provider to access tissue swelling information of the user device 310 and thereby remotely monitor the tissue swelling condition of the user 301. In some embodiments, the system 300 may be configured to alert the healthcare provider of an extreme swelling condition or trend. In embodiments in which the external entity 330 is a cloud computing environment, the user device 310 may include a communication interface, such as a wireless transceiver, that is configured to transmit and receive data communication messages, which may include data obtained or otherwise detected by sensor(s) of the wearable device 100 as discussed herein.

In some embodiments, the system 300 may include access to an electronic medical record (EMR) of the user 301. In such embodiments, the EMR may automatically record tissue swelling information for review by the healthcare provider at a future consultation with the user 301, for example.

Those of skill in the art will appreciate that the system 300 may contain other architectural modules that are not described herein. In addition, conventional elements, such as firewalls, authentication systems, payment processing systems, network management tools, load balancers, and so forth are not shown as they are not material to the invention. The system 300 may be implemented using a single user device 310 or a network of computers, including cloud-based computer implementations.

The logic 311, which may be stored on a non-transitory computer readable storage medium, includes executable instructions that when executed by one or more processors causes the one or more processors to perform operations of a computerized method 350 which may include all or a subset of the steps depicted in FIG. 3B and described below.

Figure 3B:
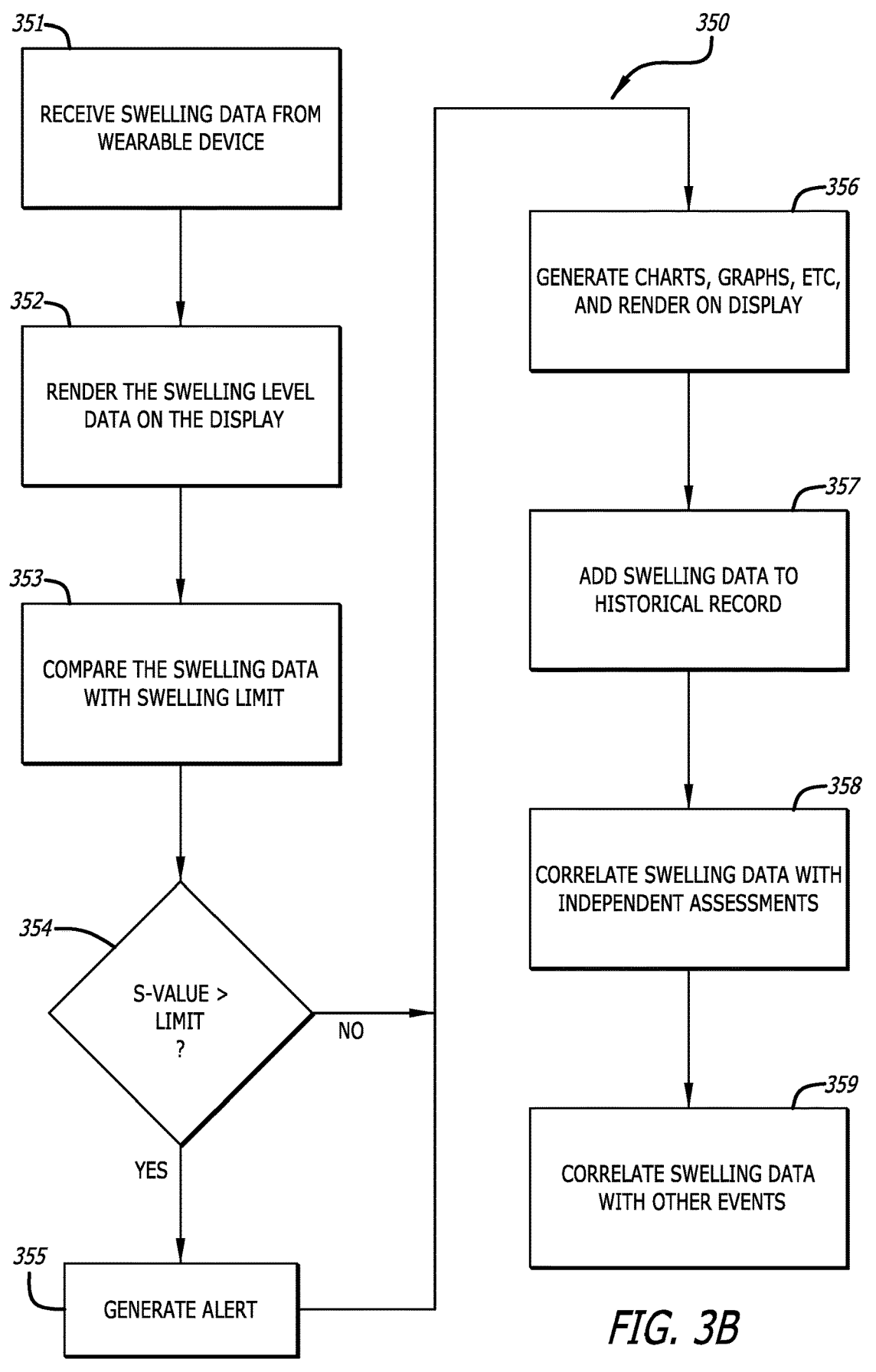

FIG. 3B illustrates a flow chart depicting the computerized method 350. The method 350 includes synchronization of the swelling data between the wearable device 100 and the user device 310 (step 351). The synchronization includes receiving swelling data from the wearable device 100 and may include transmitting swelling information to the wearable device 100.

After synchronization, the swelling data may be rendered on a display of the user device 310 (step 352) in accordance with a swelling scale level. The swelling scale may include swelling level categories (e.g., low, medium, high, and the like) and the logic 311 may assign the received swelling data a swelling level. The method 350 includes rendering the received swelling data including the swelling level on the display of the user device 310.

In some embodiments, the method 350 may include comparing the received swelling data with a swelling limit (step 353) stored in memory. As a result of the comparison (step 354), the logic 311 may generate an alert (step 355). The alert may include causing the user device to sound an audio alarm and/or transmitting a message of alert to the external entity 330.

The method 350 may further include generating and displaying charts, tables, graphs, or other visual depictions of the swelling data in the context of history, trends, urgency, standard swelling scales, and the like (step 356). In some embodiments, the depictions may include colored portions.

The method 350 may also include maintaining a record of swelling data (step 357). As such, the user 301 may review the historical swelling data. A review of historical swelling data may be advantageous in correlating swelling conditions with historical events such as illness, injury, etc.

In some embodiments, the method 350 may include calibration/correlation processes according to a machine learning module 313 of the logic 311 (step 358). The machine learning module 313 may be configured to correlate the tissue swelling data with one or more independent tissue swelling assessments. In other words, the machine learning module 313 may calibrate the wearable device 100 in accordance with the independent tissue swelling assessments, such as a swelling assessment performed by a healthcare provider. By way of example, the system 300 may include a default swelling scale and swelling data may be displayed according to the default scale. Over time, the results of multiple independent swelling assessments (measurements) may be input into the user device 310. The machine learning module 313 may continually correlate each of the independent swelling assessments with corresponding swelling data from the wearable device 100. As a result of the correlation, the machine learning module 313 may adjust the default scale levels to be align with the scale levels of the system 300 with a combination of the scale levels of the multiple independent swelling assessments. As such, a "high" swelling level of the system 300 may align with a "high" level of the multiple independent swelling assessments, for example. In some embodiments, the machine learning module 313 may correlate/calibrate the tissue swelling data with an established edema index.

By way of example, the multiple independent swelling assessments may include a circumference measurement of an extremity 60, a visual appearance, or a comfort level of a pair of shoes. In some instances, the user 301 may obtain an independent swelling assessment from a healthcare provider. In each of these scenarios, the machine learning module 313 may associate the independent swelling information with swelling data from the wearable device 100 to improve the calibration of the wearable device 100 or improve the correlation of the swelling data acquired from the wearable device 100 with independent swelling assessments. As such, the user 301 and the healthcare provider 330 may gain increased confidence in the tissue swelling data of the wearable device 100. In some embodiments, the calibrated/correlated swelling scale of the system 300 may be transmitted to or otherwise synchronized with the wearable device 100 so that the system 300 and the wearable device 100 may display swelling data in accordance with the same swelling scale.

In some embodiments, the method 350 may include a correlation process (step 359) so that the system 300 may correlate the swelling data acquired from the wearable device 100 with other user experiences, situations, or conditions. For example, the user may input a diet program and the correlation process 359 may correlate the swelling data from the wearable device 100 with the diet program. Other user experiences/conditions may also be input for correlation, such as injury, illness, stress level, allergies, and the like, for correlation with swelling data. Additional user experiences/conditions may include fluid intake/output, body weight, premenstrual period, pregnancy, movement/lack of movement, and the like. In this way, the system 300 may help identify one or more causes of tissue swelling. The system may also include correlation processes capable of assessing or projecting a state of one or more of tissue swelling causes.

Figure 3C:
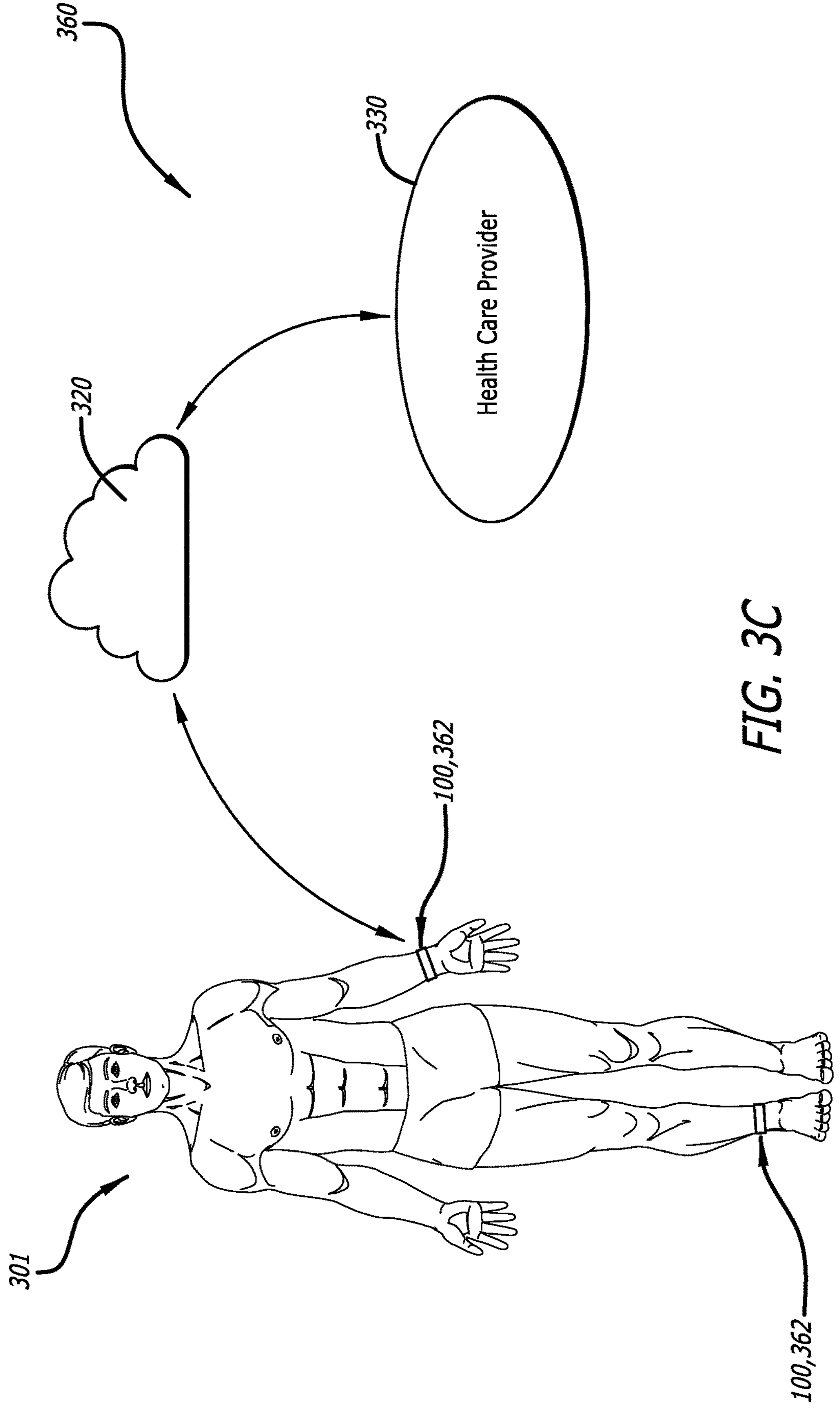
FIG. 3C illustrates a second exemplary embodiment of a system for monitoring tissue swelling incorporating the wearable device of FIG. 1, in accordance with some embodiments disclosed herein.

FIG. 3C illustrates second exemplary embodiment of a tissue swelling management system including an architecture as illustrated. The architecture of the system 360 may include the wearable device 100 including logic 362 operating thereon. In some instances, the system 360 may include the network 320 and the external entity 330 as discussed above; however, such are not required. In some embodiments, the system 360 may include more than one wearable device 100.

In some embodiments, the logic 362 may be in the form of a software application that is loaded on the wearable device 100 and executable by hardware processing circuitry similarly included therein. In other embodiments, the logic 362, or a portion thereof, need not be loaded on the wearable device 100 but may instead execute within a cloud computing environment (which may also be represented by the reference numeral 320) such that swelling data obtained or otherwise detected by sensor(s) of the wearable device 100 are communicated to the logic 362 for processing. Thus, any logic 362 represented as being part of the wearable device 100 may include an application programming interface (API) that is configured to transmit and receive data communication messages to and from the logic 362 operating in the cloud computing environment. As a result, the system 360 of FIG. 3C may be utilized for processing any swelling data obtained by sensor(s) of the wearable device 100 without any need for coupling with a user device. Thus, the wearable device 100 may obtain swelling data via sensor(s) included therein, process the swelling data with the logic 362 and hardware circuitry, and provide a notification to the user as described above. In some instances, the logic 362 may generate an alert. Examples of the alert may be, but are not limited or restricted to, (i) a sound, (ii) a visual indication such as a color change of the wearable device 100, a change of state of a light (e.g., off to on, or vice versa), or text or graphical indication displayed on a display screen of the wearable device 100 in some embodiments, or (iii) vibration directly from the wearable device 100. In some embodiments, the logic 362 of FIG. 3C may perform many of the same operations as disclosed in FIG. 3B.

Figure 4:
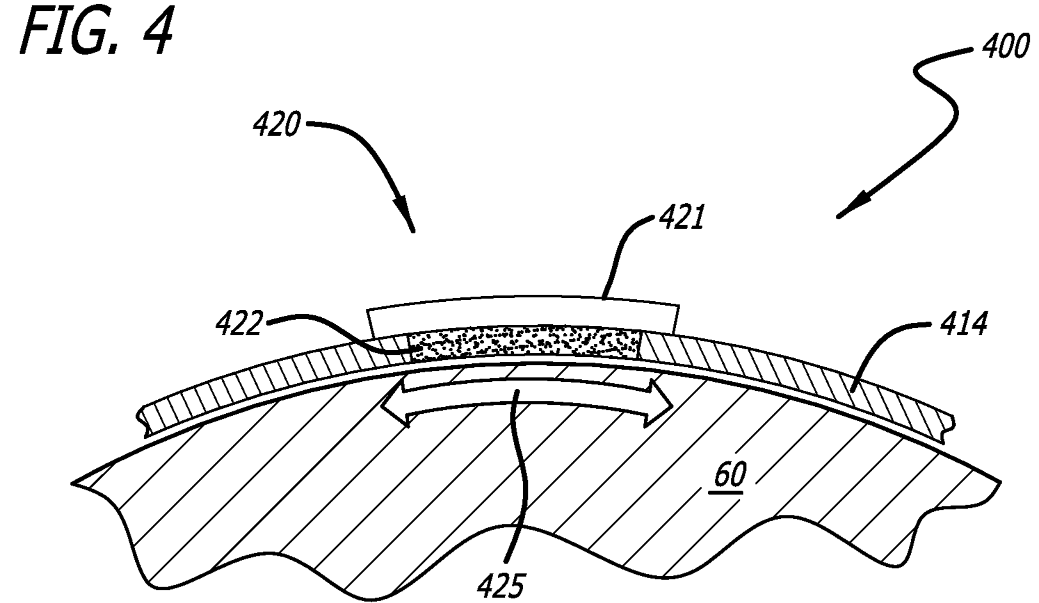
FIG. 4 is an illustration of a wearable device including a strain-based swelling sensing mechanism, in accordance with some embodiments disclosed herein.

FIG. 4 illustrates an exemplary wearable device 400 including a strain-based sensing mechanism 420. The band 414 extends along a circumference of the extremity 60. The sensing mechanism 420 includes a strain sensor 421 (e.g., a strain gauge) and stretchable portion 422 of the band 414. The sensor 421 is coupled to the band 414 so as to extend across the stretchable portion 422 so that the sensor 421 can assess a strain 425 (i.e., deformation or length increase) of the stretchable portion 422. In some embodiments, the band 414 may be generally non-stretchable so that the strain 425 is defined by (or at least correlates with) an increase in the circumference of the extremity 60 due to tissue swelling. The sensor 421 is coupled to the console 130 to provide electrical signals to the console 130 in accordance with strain 425. In use, the user may apply the wearable device 400 to the extremity 60 such that at least some strain 425 is present along the stretchable portion 422 to define a strain value as detected by the strain sensor 421. In some instances, applying the wearable device 400 may include adjusting a loop length of the band 414.

Figure 5:
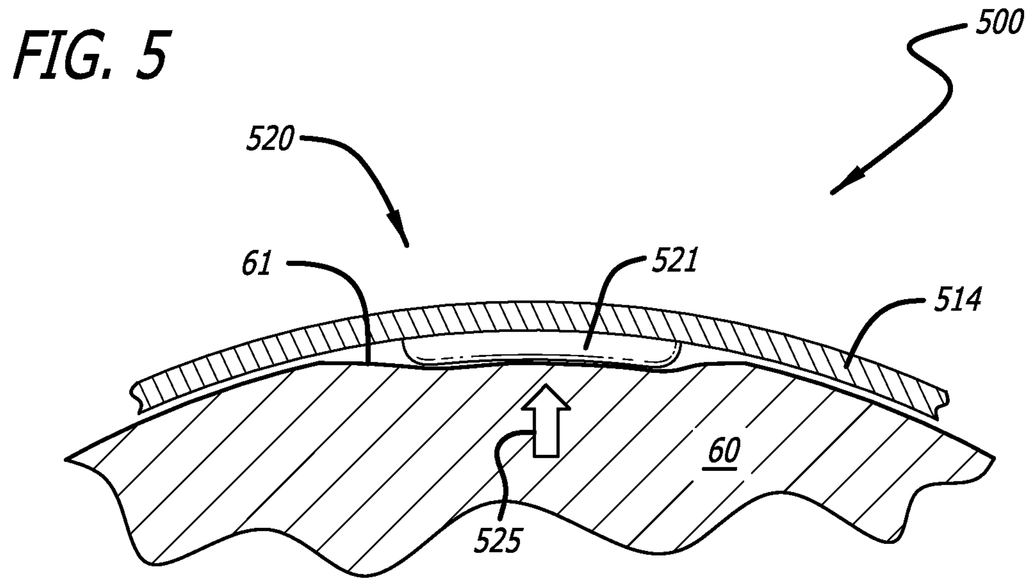
FIG. 5 is an illustration of a wearable device including a pressure-based swelling sensing mechanism, in accordance with some embodiments disclosed herein.

FIG. 5 illustrates an exemplary wearable device 500 including a pressure-based sensing mechanism 520. The wearable device 500 may be applied to an extremity 60 such as an arm or a leg. The band 514 extends along a circumference of the extremity 60. The sensing mechanism 520 includes a pressure sensor 521 (e.g., a thin film pressure sensor) disposed between the band 514 and the skin 61. The sensor 521 is configured to assess a pressure 525 (or a force) exerted on the sensor 521 by the skin 61. In some embodiments, the band 514 may be generally non-stretchable so that the pressure 525 exerted on the sensor 521 is defined by (or at least correlates with) a pressure adjacent the skin 61 of the extremity 60 due to tissue swelling. The sensor 521 is coupled to the console 130 to provide electrical signals to the console 130 in accordance with pressure 525. In use, the user may apply the wearable device 500 to the extremity 60 such that at least some pressure is exerted on the sensor 521. In some instances, applying the wearable device 500 may include adjusting a loop length of the band 514.

Figure 6A:
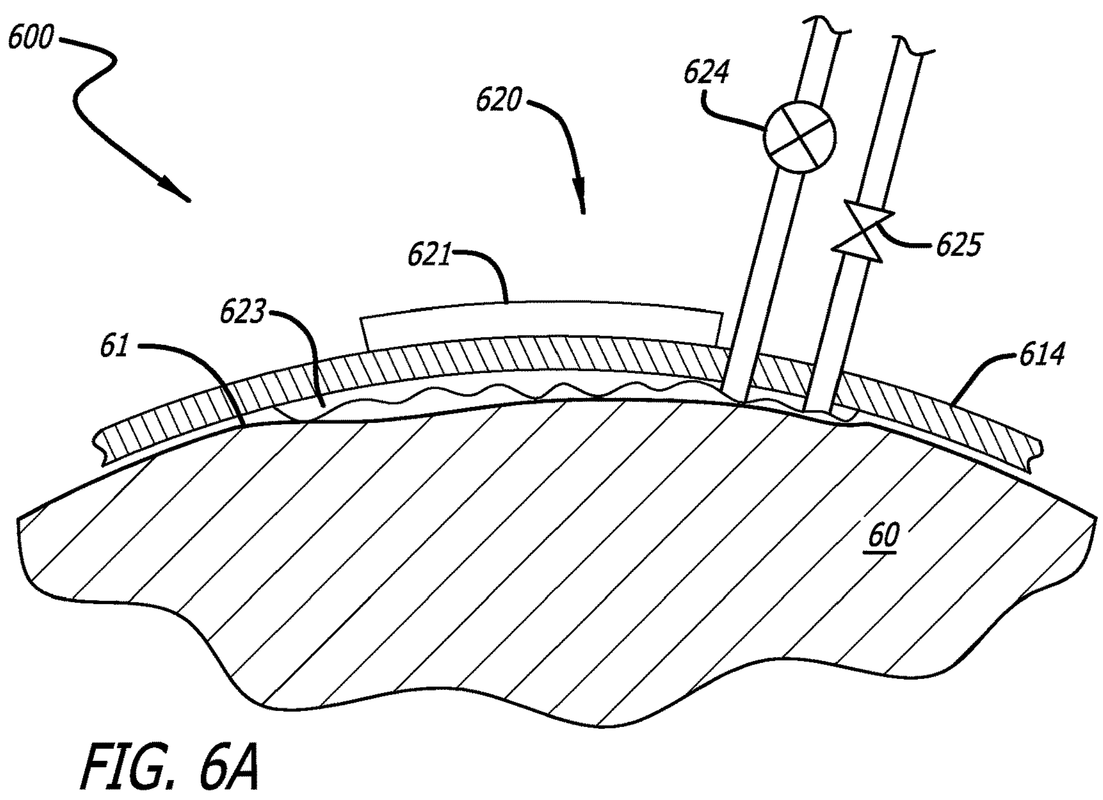
FIG. 6A is an illustration of a wearable device including a depression-based swelling sensing mechanism showing the tissue in a non-depressed state, in accordance with some embodiments disclosed herein.
Figure 6B:
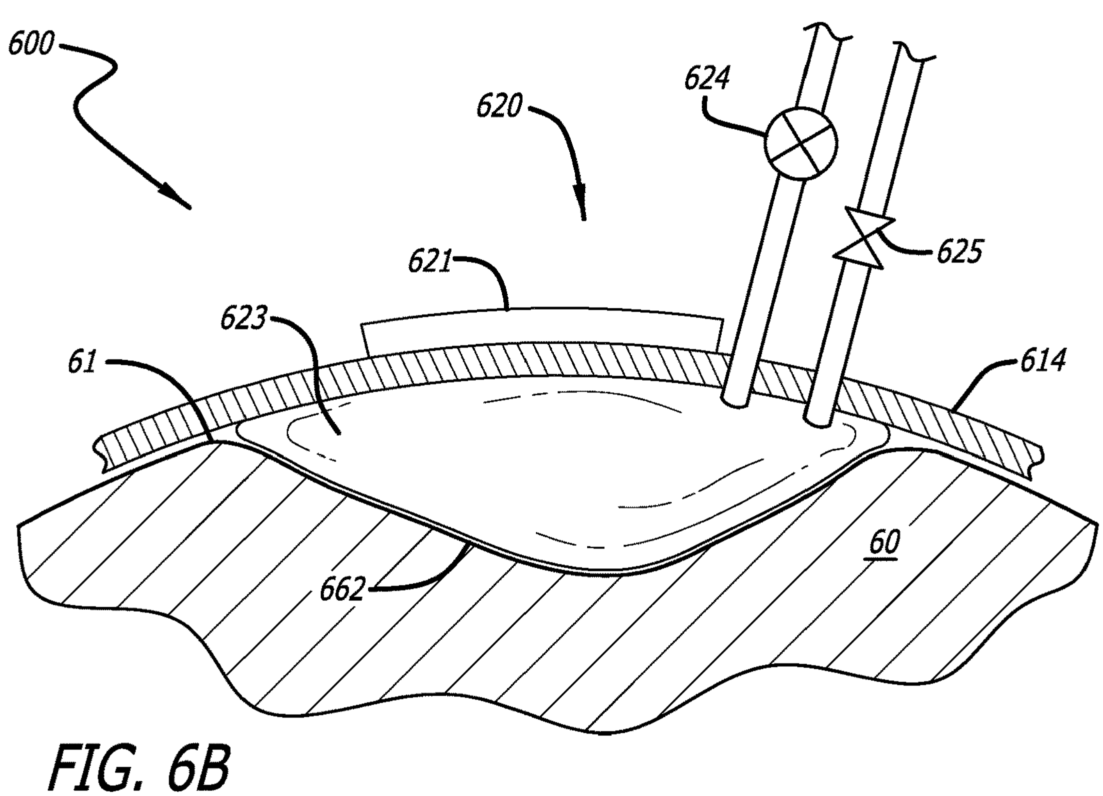
FIG. 6B is an illustration of the wearable device of FIG. 6A including a depression-based swelling sensing mechanism shown in a depressed state, in accordance with some embodiments disclosed herein.

FIGS. 6A and 6B illustrate an exemplary wearable device 600 including a depression-based sensing mechanism 620. The wearable device 600 may be applied to an extremity 60 such as an arm or a leg. The band 614 extends along a circumference of the extremity 60. The sensing mechanism 620 is configured to assess a swelling condition of the extremity 60 via a depression recovery process. Functionally speaking, the sensing mechanism 620 is configured to define a tissue depression and then measure a rate of depression recovery. FIG. 6A illustrates the device 600 as it may be initially applied to the extremity 60, and FIG. 6B illustrates the device 600 defining the depression 662.

The sensing mechanism 620 includes a proximity sensor 621 configured to measure a depth of the depression (i.e., a separation distance between the sensor 621 and the skin 61). A pump 624 supplies air to a bladder 623 disposed between the band 614 and the skin 61 to define the tissue depression 662. A valve 625 vents air from the bladder 623 to allow the depression 662 to recover. During depression recovery, the proximity sensor 621 provides electrical signals to the console 130 corresponding to depression depth measurements.

In use, the user applies the wearable device 600 to the extremity 60 with the bladder 623 in a deflated state as shown in FIG. 6A. The pump 624 is activated to define the depression 662 after which the pump 624 is deactivated. The valve 625 is activated to allow air to flow out of the bladder 623 and thereby allow the depression 662 to recovery toward the non-depressed state. As the depression recovers, the sensor 621 measures the depth of the depression. The swelling logic 131 may activate and deactivate the pump 642, and may also actuate and de-actuate the valve 625. The swelling logic 131 acquires measurement data from the sensor 621 to determine a recovery rate of the depression 662.

In some embodiments, the tissue depression 662 may be defined by an extendable protrusion coupled with an electromechanical displacement device (e.g., a motor or a solenoid). In other embodiments, the depression may be defined manually by the pressing on a portion of the wearable device 600. The foregoing are just a few examples of defining the tissue depression 662. Although not shown or described, other mechanisms for defining the tissue depression 662 may be contemplated by one of ordinary skill and are therefore included in this disclosure. Similarly, the depth of the tissue depression 662 may be assessed by various proximity assessment technologies, such as optical, sonic, capacitance, inductance, magnetic or the like. These and any other proximity assessment technologies as may be contemplated by one of ordinary skill are included in this disclosure.

Figure 7:
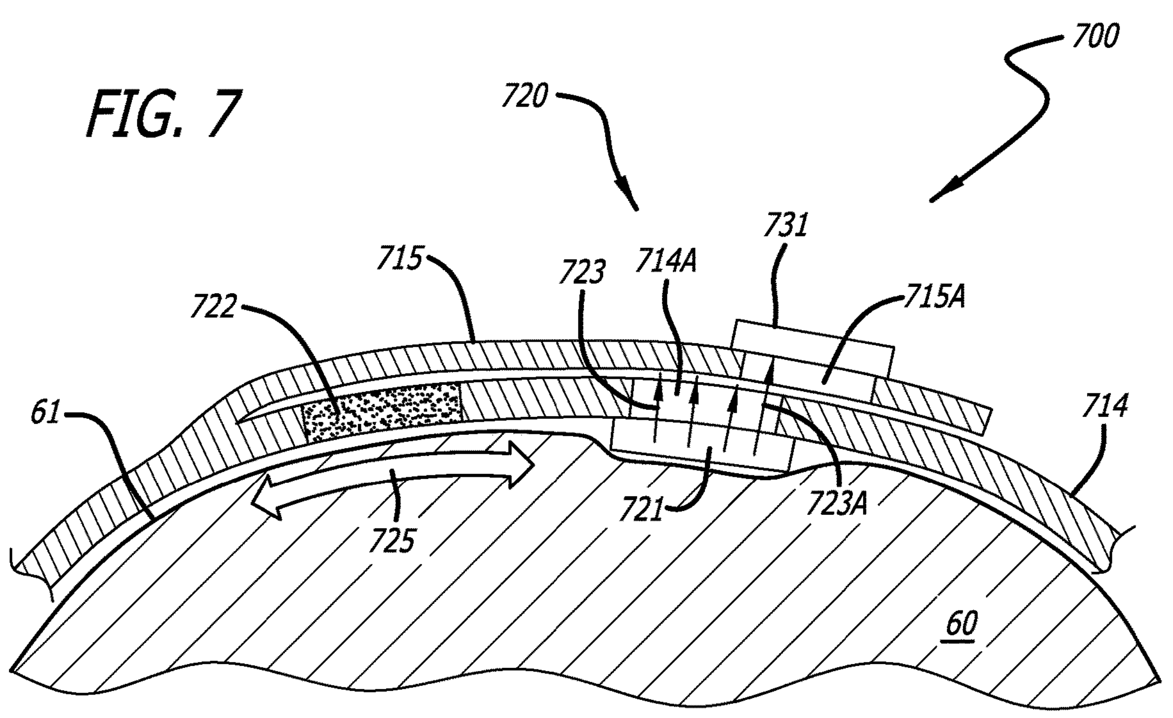
FIG. 7 is an illustration of a wearable device including a light-based swelling sensing mechanism, in accordance with some embodiments disclosed herein.

FIG. 7 illustrates an exemplary wearable device 700 including a light-based sensing mechanism 720. The band 714 extends along a circumference of the extremity 60 and includes a stretchable portion 722. The band 714 may be generally non-stretchable so that the strain 725 of the stretchable portion 722 is defined by (or at least correlates with) an increase in the circumference of the extremity 60 due to swelling. The light-based sensing mechanism 720 is configured to provide an electrical signal in accordance with the strain 725. The sensing mechanism 720 includes a light source 721 (e.g., a light emitting diode (LED), an LED array or any other suitable light source) and photo sensor 731. The light source 721 is coupled with the band 714 so as to emit light 723 through a first opening 714A extending though the band 714, and the photo sensor 731 is coupled to an overlapping portion 715 of the band 714 so as to receive light 723 through a second opening 715A extending through the overlapping portion 715. The first opening 714A and the second opening 715A are sized and positioned so that an overlapping portion of the first and second openings 714A, 715A varies in accordance with the strain 725. In other words, the overlapping portion 715 is displaced with respect to the band 714 in accordance with the strain 725. As the strain 725 increases, an increased portion of the first opening 714A overlaps second opening 715A. The sensing mechanism 720 is configured so that the photo sensor 731 receives a varying portion 723A of the light 723 passing through the overlapping portion of the first and second openings 714A, 715A. In alternative embodiments, the light source 721 may be coupled with the overlapping portion 715 and photo sensor 731 may be coupled with the band 714.

Figure 8:
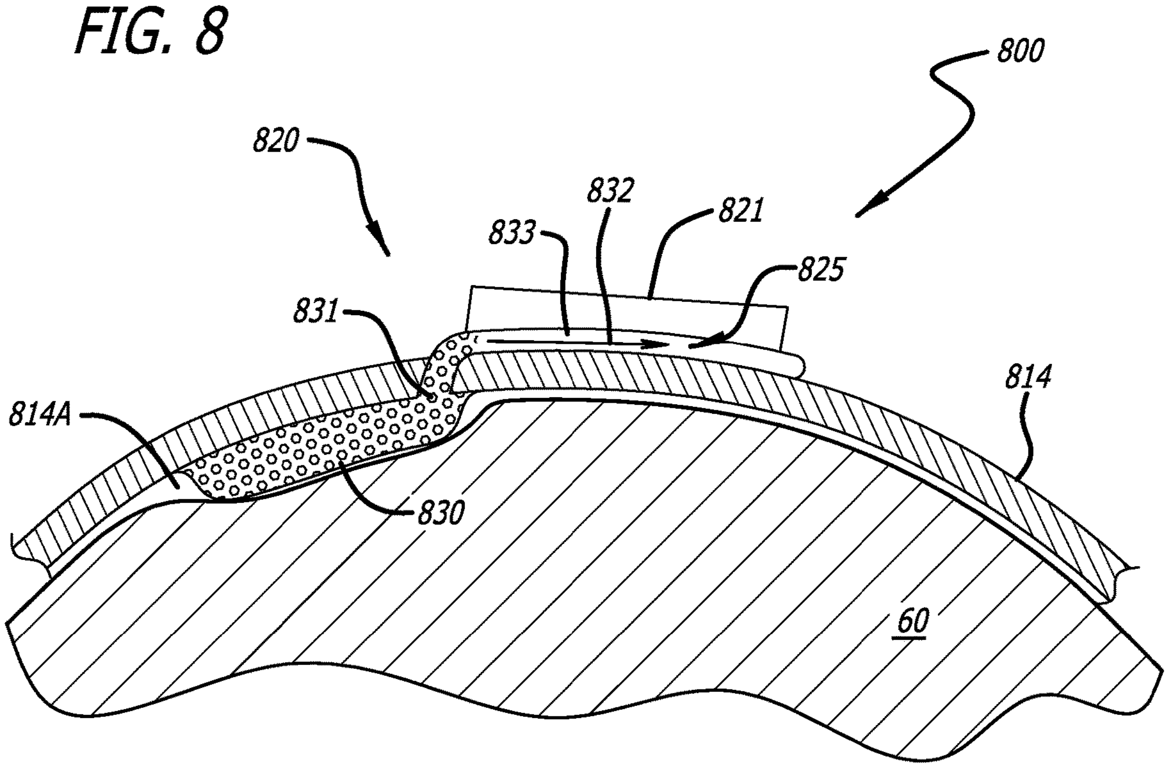
FIG. 8 is an illustration of a wearable device including a fluid-based swelling sensing mechanism, in accordance with some embodiments disclosed herein.

FIG. 8 illustrates an exemplary wearable device 800 including a fluid-based sensing mechanism 820. The band 814 extends along a circumference of the extremity 60. The band 814 may be generally non-stretchable so that a space 814A between the extremity 60 and the band 814 is defined or at least correlates with swelling of the extremity 60. The fluid-based sensing mechanism 820 is configured to provide an electrical signal in accordance with a variation in the space 814A. The sensing mechanism 820 includes a fluid bladder 830 containing a fluid 831, and the fluid bladder 830 is disposed within the space 814A. In some embodiments, the fluid 831 may be a liquid and in further embodiments, the fluid 831 may have at least one electrical property, such as conductance, for example. The fluid bladder 830 is in fluid communication with a fluid channel 833 and the fluid 831 may be variably disposed within the fluid channel 833. More specifically, the fluid 831 flows along the channel 833 as indicated by the arrow 832 as the fluid bladder 830 is compressed.

In some embodiments, the fluid channel 833 may be disposed on an outside surface of the band 814. A sensor 821 is operatively coupled to the fluid channel 833 so that a signal 825 of the sensor 821 correlates with a volume of the fluid 831 within the fluid channel 833. In some embodiments, the sensor 821 may be a capacitive sensor configured detect a signal 825 in the form of an electrical capacitance of the fluid channel 833. In other embodiments, the signal 825 may an electrical inductance or resistance. In still other embodiments, the signal 825 may be sonic or optical parameters. By way of summary, swelling of the extremity 60 may cause to the fluid bladder 830 to collapse forcing fluid 831 into the fluid channel 833. The increased fluid 831 within the fluid channel 833 generates a difference in the signal 825 of the fluid channel 833 to be detected by the sensor 821. In other words, the signal 825 as detected by the sensor 821 corresponds to the swelling condition of the user.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A wearable device for monitoring a tissue swelling condition of a user, comprising:
- a device attachment mechanism for securing the wearable device to a body of the user;
- a sensing mechanism coupled to the device attachment mechanism, the sensing mechanism configured to provide an electrical signal in accordance with the tissue swelling condition; and
- a console including one or more processors and logic, that, upon execution by the one or more processors, causes performance of operations including:
- receiving the electrical signal from the sensing mechanism, and
- providing swelling information to the user in accordance with the electrical signal, wherein the device attachment mechanism comprises:
- a light sensor operatively coupled with a light source, and
- a variable aperture disposed between the light source and the light sensor, wherein:
  - the variable aperture varies in accordance with a length of a stretchable portion of the device attachment mechanism, and
  - the light sensor provides the electrical signal in accordance with an amount of light from the light source passing through the variable aperture to the light sensor.

2. The device of claim 1, wherein the device attachment mechanism comprises a band configured to extend around an extremity of the user.

3. The device of claim 1, wherein the device attachment mechanism is configured to extend around an ankle or a wrist of the user.

4. The device of claim 1, wherein the variable aperture comprises:
- a first opening extending through a first portion of the device attachment mechanism; and
- a second opening extending through a second portion of the device attachment mechanism, wherein:
  - the first portion overlaps the second portion,
  - the first portion and the second portion are coupled to opposite ends of the stretchable portion of the device attachment mechanism, so that the second portion is displaced relative to the first portion in accordance with a change in the length of the stretchable portion, and
  - the first opening and the second opening are positioned to variably overlap in accordance with the relative displacement between the second portion and the first portion to define the variable aperture.

5. The device of claim 1, wherein attachment mechanism is configured to secure the wearable device to the body of the user via one or more adhesive portions.

6. The device of claim 1, wherein the logic comprises a swelling logic module stored in memory, the swelling logic module configured to:
- compare swelling data with a swelling limit stored in memory, and
- as a result of the comparison, provide an alert to the user.

7. The device of claim 6, wherein the logic comprises a correlation module stored in memory, the correlation module configured to:
- receive independent tissue swelling assessments as input by the user,
- correlate the swelling data with the independent tissue swelling assessments, and
- display swelling information in accordance with the correlation.

8. The device of claim 1, wherein the one or more processors are included within cloud computing resources.

9. A system for monitoring tissue swelling of the user, comprising:
- the wearable device of claim 1; and
- a non-transitory computer-readable storage medium (CRM) including executable instructions that when executed by one or more processors causes the one or more processors to perform operations, comprising:
  - receiving tissue swelling data from the wearable device; and
  - rendering tissue swelling information on a display.

10. The system of claim 9, wherein the CRM is stored on a cellular phone.

11. The system of claim 9, wherein the operations further comprise comparing the tissue swelling data with a swelling limit of the CRM.

12. The system of claim 11, wherein as a result of the comparison, the operations further comprise generating a user alert.

13. The system of claim 9, wherein the operations further comprise maintaining a historical record of the tissue swelling data.

14. The system of claim 13, wherein the operations further comprise rendering a chart on the display, the chart illustrating at least a portion of the historical record of the tissue swelling data.

15. The system of claim 9, wherein the operations further comprise:

receiving independent tissue swelling assessments as input by the user;

correlating the tissue swelling data to the independent tissue swelling assessments; and displaying swelling information in accordance with the correlation.

16. The system of claim 9, wherein the operations further comprise:

receiving historical user event information as input by the user, the historical user event information including one or more user events;

correlating the tissue swelling data with the one or more user events; and displaying historical swelling information in combination with the historical user event information.

17. The system of claim 9, wherein the operations further comprise transmitting user information across a network to an external entity.

18. The system of claim 17, wherein the external entity is a healthcare provider for the user.

* * * * *